United States Patent [19]

Oliver et al.

[11] Patent Number: 4,919,664

[45] Date of Patent: Apr. 24, 1990

[54] STIMULATION OF HAIR GROWTH

[76] Inventors: Roy F. Oliver; Colin A. B. Jahoda, both of Department of Biological Sciences University of Dundee, Dundee, Great Britain, DD1

[21] Appl. No.: 16,224

[22] Filed: Feb. 19, 1987

[30] Foreign Application Priority Data

Feb. 21, 1986 [GB] United Kingdom ................ 8604360

[51] Int. Cl.$^5$ ............................................. A61F 2/10
[52] U.S. Cl. ..................................................... 623/15
[58] Field of Search ..................... 623/1, 2, 11, 12, 15, 623/16, 8; 128/1 R; 435/240.25

[56] References Cited

U.S. PATENT DOCUMENTS

| | | | |
|---|---|---|---|
| 4,185,618 | 1/1980 | Corey | 128/1 R |
| 4,353,888 | 10/1982 | Sefton | 623/11 |
| 4,391,909 | 7/1983 | Lim | 623/11 |
| 4,418,691 | 12/1983 | Yannas et al. | 623/15 |
| 4,442,655 | 4/1984 | Stroetmann | 623/11 |
| 4,508,819 | 4/1985 | Rose | 128/1 R |
| 4,661,447 | 4/1987 | Fabricius et al. | 435/240.25 |
| 4,677,968 | 7/1987 | Krueger | 128/1 R |
| 4,721,096 | 1/1988 | Naughton et al. | 128/1 R |
| 4,742,120 | 2/1987 | Nevo et al. | 623/15 |

FOREIGN PATENT DOCUMENTS 0013394 7/1980 European Pat. Off. .
0107885 5/1984 European Pat. Off. .

OTHER PUBLICATIONS

Jahoda et al., Vibrissa Dermal Papilla Cell Aggregative Behaviour in vivo and in vitro, J. Embryol. Exp. Morph., 79, 211–224 (1984).

Jahoda et al., Introduction of Hair Growth by Implantation of Cultured Dermal Papilla Cells, Nature, vol. 311, No. 5986, pp. 560–562, Oct. 1984.

Primary Examiner—Richard J. Apley
Assistant Examiner—David J. Isabella
Attorney, Agent, or Firm—Kareem M. Irfan

[57] ABSTRACT

The present invention relates to a method of stimulating hair growth in part of the skin of a mammal. The method comprises selecting lower follicular dermal cells and culturing them. An opening is then formed in the skin and the cultured dermal cells introduced through the opening in the outer epidermis layer of the skin into contact with the dermis, with said cultured dermal cells in association with epidermis cells.

The invention also provides a hair growth stimulating combination comprising cultured lower follicular dermal cells in admixture with epidermis cells, as well as such cultured dermal cells for use in the preparation of an injection composition for stimulating hair growth in human skin.

14 Claims, No Drawings

STIMULATION OF HAIR GROWTH

The present invention relates to the stimulation of hair growth in mammals and especially humans.

Many diverse treatments have been previously proposed for the restoration of hair to areas of skin, in particular areas of human scalp, which have suffered hair loss. The vast majority of these have little or no effect. One of the less ineffective treatments which is available commercially comprises the physical transplantation of complete pieces of scalp including the whole roots of hairs with the surrounding dermis and epidermis from scalp areas in which hair loss has not occurred to areas where hair loss has occurred in order to produce hair growth thereat. A major limitation of this form of treatment is though that each new hair follicle requires the transplantation of a complete existing hair follicle together with its surrounding skin tissue. Thus the technique is limited by the available quantity of hair bearing skin. Also the procedure is extremely tedious and time-consuming both for the subject under treatment and for the operative requiring very precise manipulation of large numbers of individual hair transplants.

More recently it has been found that cultured dermal papilla cells when associated in vitro with non-hair-forming embryonic epidermis from mice can induce hair follicle formation. This procedure involves though first obtaining suitable embryonic tissue which would normally be available for humans and certainly not from the individual human suffering hair loss. It would then be necessary to culture the embryonic epidermal cells and then add these to the cultured dermal papilla cells prior to implantation.

It is an object of the present invention to avoid or minimize on or more of the above disadvantages.

It has now surprisingly been found that new hair growth can be stimulated in human scalp by introducing cultured dermal papilla cells alone into the dermis in association with epidermal cells which may be those already present at the treatment site or may be directly or indirectly obtained from other parts of the scalp.

The present invention provides a method of stimulating hair growth of a desired hair type in part of the skin of a mammal which method comprises the steps of: selecting at least one lower follicular dermal cell of said desired hair type; culturing the selected dermal cell so as to produce cultured dermal cells; forming an opening in the skin of said part of the mammal; and introducing cultured dermal cells through said opening in the epidermis into contact with the dermis in proximity to the epidermis and with said cultured dermal cells in association with epidermal cells.

With the method of the present invention new hair follicle development and hair growth can appear within a period of a few weeks in the immediate vicinity of the implantation site and continues thereafter in what appears to be a substantially normal manner.

As indicated above, the method of the present invention involves use of lower follicular dermal cells of the desired hair type. THus for stimulating hair growth on the scalp, there are used dermal cells originating from human scalp, preferably from the scalp of the subject being treated. In this way, the hair colour, and physical size, texture and configuration will most closely match any existing hair growth on the scalp of the subject. Various dermal cells may moreover be used in the method of the invention including those from the dermal sheath as well as those from dermal papilla, the latter being preferred.

Various methods are already known in the art for culturing dermal papilla cells and other lower follicular dermal cells as described for example in Jahoda and Oliver (1981 British Journal of Dermatology 105 623-627 and 1984 J. Embryol. Exp. Morph 79 211-224). In general the dermal cells are cultured in a suitable culture medium. Preferably there is used a so called "defined" medium i.e. a medium in which only specific known components are present, in preference to other media which contain components of uncertain indentity such as for example foetal calf serum.

Desirably the culture medium includes one or more dermal cell culture promoting and growth factors such as for example fibroblast, epidermal, and platelet derived growth factors. One particularly suitable medium containing a number of growth factors that may be mentioned is "Chang's Medium" (H Chang et al Proc. Nat. Acad. Sci. (USA) (1982) 79 4795-4799 available from Hana Media Inc. Berkley, Cal. USA)

In order to maintain a significant level of hair growth stimulating activity, the number of passages of the culture is desirably limited, for example to 4 passages, and/or there are desirably used cloned dermal cell cultures wherein is used a cultured dermal cell population which originates from a single individual dermal cell.

The cultured dermal cells are preferably used in a form substantially free of non-dermal cellular material and thus the method of the invention preferably includes the step of separating cultured dermal cells from cell culture and/or support medium prior to introduction of the cultured cells into the skin.

The invention also provides cultured human scalp lower follicular dermal cells for use in the preparation of a hair growth stimulating injection composition. Preferably the cultured dermal cells are recovered from the culture system by physical means without the use of enzymes such as trypsin whereby the cell membranes and attached extra-cellular material in particular are substantially non-degraded and in a relatively adhesive form. Nevertheless where it is desired to implant the cultured cells by injection the cells may be collected using such enzymes and presented in a relatively mobile form in a physiologically acceptable liquid injection vehicle.

Advantageously, the cultured dermal cells are subjected to physical and/or bio-chemical aggregation in order to induce and/or maintain aggregation of the cultured dermal cells in the skin at the treatment site thereby to enhance inter-action with the epidermal cells. Thus, for example, the use of centrifugation during recovery of the cultured dermal cells will end to result in a degree of aggregation. In addition there may be added to the cultured dermal cells at the time of introduction to the dermis or before, a suitable aggregation enhancing substance for example a glycoprotein such as fibronectin or glycosaminoglycans e.g. dermatan sulphate, chondroitin sulphates, proteoglycans, heparan sulphate, and other extracellar matrix components known to bind dermal papilla cells e.g. collagens, hormones, and growth factors known to induce aggegative behaviour.

The cultured dermal cells may be introduced into contact with the dermis and in association with epidermal cells in any suitable manner. Thus for example, the cultured dermal cells may be introduced directly between the dermis and the epidermis of the outer skin layer at a treatment site. This may conveniently be effected by raising a blister on the skin at the treatment site and introducing the dermal cells inside the blister ie into the cavity occupied by the blister fluid. The blister may be raised by any suitable means including for example by mechanical means such as the application of a reduced pressure suction to the skin, or by chemical means.

Alternatively the cultured dermal cells may be introduced into a suitable incision extending through the epidermis down into the dermis, the incision being filled up with cultured dermal cells generally up to a level in direct proximity to the epidermis at either side of said incision.

In yet another alternative, the cultured dermal cells may be introduced together with epidermal cells. The epidermal cells may either be in the form of free epidermal cells or in the form of a sheet of epidermal cells obtained for example from another part of the subject's body eg the thigh. In the latter case the dermal cells are conveniently enclosed in a pocket formed from the sheet of epidermis. In the former case, the epidermal cells may conveniently be cultured epidermal cells, and desirably obtained from the subject undergoing treatment. Both procedures have the advantage that they avoid the need for introducing the cultured dermal cells into the dermis at a carefully selected position in more or less direct proximity to the adjoining epidermis of the subject's skin at the treatment site. This considerably simplifies the treatment procedure since with this approach, the cultured dermal cells ma be introduced into the dermis at a position which is not in direct proximity to the epidermis of the outer skin layer. Where the cultured dermal cells are introduced inside a pocket formed of epidermis, the incision in the skin at the treatment site is desirably formed so as to extend obliquely at a more or less shallow angle to the surface of the skin so as to form in effect a flap of skin under which the pocket of cultured dermal cells may be introduced, the flap then being positioned back over the top of the pocket to seal it in and protect it from external contamination.

Preferably a large plurality of small closely spaced openings are formed in said part of the skin and the cultured dermal cells introduced thereinto. Desirably each opening is filled with a large plurality of cultured dermal cells. The size and depth of the openings may be readily varied. Desirably though the lateral extent of individual openings is minimized and preferably limited to about 5 mm, most preferably 2 mm. The depth of the openings is desirably greater than the full depth of the epidermis (though this is not normally required where the opening is being made at a blister as described above), and advantageously extends at least 1 mm, preferably at least 3 mm into the dermis.

The openings in the skin may be formed by any suitable means and will generally use some form of skin cutting instrument such as a scalpel or a hypodermic needle. Advantageously though there is used a multiple-perforation apparatus having a plurality of spaced apart cutting edges formed and arranged for simultaneously forming a plurality of spaced apart openings in the skin.

In another aspect the present invention provides human cultured human scalp lower follicular dermal cells for use in the preparation of a hair growth stimulating injection composition.

Conveniently the cultured dermal papilla cells are introduced simultaneously into a plurality, preferably at least several, openings in the skin.

The quantity of cells introduced into each opening will depend on various factors such as the size and depth of the opening and the overall viability and activity of the cells. In general though there is used an amount of from 1000 to 1,000,000 eg. from 10,000 to 200,000 cells per opening in a volume of 0.5 to 50 $\mu l$.

Advantageously the subject is treated, topically and-/or systematically before or at the same time, but preferably after treatment with the dermal cells with a hair growth promoting substance in order to enhance the new hair growth. Suitable substances that may be mentioned include minoxidil (available from the Upjohn Co. of Kalamazoo USA), cyclosporin, and natural or synthetic steroid hormones and their enhancers and antagonists eg. anti-androgens.

Further preferred features and advantages of the present invention will appear from the following detailed examples given by way of illustrative only of some preferred embodiments.

EXAMPLE 1

Growth of Rat Vibrissia Hairs

Preparation of Cultured Dermal Papilla Cells

Dermal Papilla Cells were obtained from inbred hooded PVGC rats (Colony, Dundee University, Scotland) using procedures described in Oliver (1966, J. Embroyol. Exp. Morph. 15, 331–347). Briefly an incision was made below the most ventral horizontal row of whiskers on the rat mystacial pad. An incision was extended dorsally by cutting parallel to the skin surface. The whisker pad was reflected and retained with artery forceps. The exposed ends of whisker roots or "bulbs" were then cut from the bases of cleaned follicles and transferred to sterile medium as described in Jahoda and Oliver (1981, British Journal of Dermatology 105, 623–627).

Primary cultures were initiated as described in Jahoda and Oliver except that the initial culture vessel used was not the Cruikshank Chamber but a 35 mm diameter plastic dish obtained from the Sterilin Company of Feltham, Middx., England. The present experiments were performed on passage 1 subcultured cells which were obtained by subculturing primary cultures after 2-3 weeks using 0.25% trypsin in phosphate-buffered saline/EDTA (0.2 mg/ml). All current implantations were performed on passage 1 cultures of rat whisker dermal papilla cells, using medium as described in Jahoda and Oliver. The foetal calf serum requirement was between 10 and 20%. Further details of the above procedures are described in Jahoda and Oliver (1984, J. Emryol. exp. Morph. 79, 211–244).

24 hours prior to implantation, the cultured cells were incubated in medium in which the feotal calf serum had been replaced by rat serum at a concentration of from 10 to 20%. The rat serum was obtained from rats of the same strain by syringe extraction from the hearts of freshly killed animals. Following removal, blood was left overnight at 4° C. to allow separation of blood cells from serum. Serum was then removed with a pasteur pipette and spun for 30 minutes in a centrifuge at at 3,000 G to remove remaining cells and debris.

PREPARATION OF HOST IMPLANTATION SITE

Rat ears were depilated using Immac (Trade Name) hair removal cream (available from Anne French of London, produced under licence from Whitehall Laboratories, New York, USA) and then washed thoroughly with warm water and swabbed with 70% alcohol. Artery forceps were used to clamp the edge of the ear in a horizontal position over a support bed of cotton wool. An incision was made of length between 1 and 3 mm and with a depth below the full thickness of the skin. The cut was made using the tip a number 11 scalpel blade. A region of the ear which contained less visible vasculature was chosen to avoid excess external bleeding. Following the cut the incision was swabbed with absorbent cotton wool until bleeding ceased.

PREPARATION OF CULTURED CELLS FOR IMPLANTATION

Cells were obtained from 35 mm culture dishes in the following manner:

culture medium was removed by pipette and the dish was then inverted to remove the maximum amount of medium. A rubber policeman (an instrument consisting of a silicon rubber cube with a wire handle) was then used to scrape the cells from the bottom of the dish. This action results in the cells forming bodies of semi-solid adhesive cellular material which are visible to the naked eye in clumps at the bottom of the dish.

IMPLANTATION OF CULTURED CELLS

Bodies of the cultured cells were picked up using number 5 sharpened watchmaker forceps. These were then transferred to the wound incision and released into the wound. This process was repeated until the wound was packed with a body of some 100,000 or so of the papilla cells often forming a convex dome above the skin surface. The ears were then left untouched, no attempt being made to cover the ears or openings therein with any dressing or other sealant.

RESULTS

The normal hair growth (average length 1-2 mm) returned to the depilated ear surface after a few weeks. Longer than normal experimental hairs which were of vibrissa-like nature were observed by 4 weeks following the implantation. Some of these induced hairs (up to 12 per implantation site) grew to a length of 6-7 mm and continued to grow some 3 to 4 months following implantation. The induced hairs were seen microscopically to emanate in a line following exactly the position of the wound opening scar. Closer observation reveals follicle openings inside the line of the scar tissue itself.

EXAMPLE 2

METHOD OF INDUCING HUMAN HAIR GROWTH

Human dermal papilla cells are collected and cultured using substantially the same procedure as described in Example 1 except that the dermal papilla cells were obtained by teasing out dermal papillae using tungsten needles from exposed hair follicles in hair-growing-scalp biopsies and the autologous human serum would be used in the growth of cells.

Further details of suitable procedures are described in Messenger (Br. J. Derm. 110 685-689 (1984).

Implantation sites are prepared as described in Example 1 and then filled with the cultured dermal papilla cells (approximately 100,000 cells per site).

EXAMPLE 3

GROWTH OF HUMAN HAIR

PREPARATION OF CULTURED DERMAL PAPILLA CELLS

Dermal papilla cells were obtained from the scalp of a female subject aged 48 years and cultured using the procedure of Example 1. Passage 1 subcultured cells were recovered from the culture medium again using similar procedures to those of Example 1, 29 days after first collection of dermal papilla cells, for use in the treatment as described below.

PREPARATION OF TREATMENT SITE

Human full thickness (epidermis and dermis skin grafts obtained from the groin of a 70 year old male subject were transplanted onto nude athymic mice.

INTRODUCTION OF CULTURED DERMAL CELLS

After 42 days small incisions were made in the skin grafts and the cultured dermal papilla cells introduced thereinto using a similar procedure to that described in Example 1.

RESULTS 60 days after introduction of the dermal papilla cells biopsies were taken from the treated mice and examined microscopically. Various stages of dermal papilla-epidermis interaction and hair growth were observed at a number of sites, including the development of a distinct basal lamina, localized epidermal hyperplasia with a pronounced membrane thickening, and formation of a hair follicle peg, at the site of dermal papilla cell introduction.

What is claimed is:

1. A method of inducing hair follicle development and hair growth of a desired hair type in part of the skin of a mammal said skin having an outer epidermis layer and an inner dermis layer, which method comprises the steps of: selecting at least one lower follicular dermal cell to provide selected dermal cell, culturing the selected dermal cell so as to produce cultured dermal cells; forming an opening in the outer epidermis layer of said part of the mammal; and introducing cultured dermal cells through said opening in the epidermis layer into contact with the dermis layer in proximity to the epidermis and with at least some of said cultured dermal cells in contact with epidermal cells.

2. A method as claimed in claim 1 wherein said cultured dermal cells are subjected to aggregation by an aggregation means thereby enhancing interaction with the epidermal cells.

3. A method as claimed in claim 2 wherein said cultured dermal cells are treated with means for causing aggregation comprising an aggregation promoting glycoprotein, or glycosaminoglycan.

4. A method as claimed in claim 1 wherein said opening is in the form of a narrow incision having a depth of from 0.4 to 6 mm.

5. A method as claimed in claim 1 which method includes the step of inducing a blister defining a blister cavity in said part of the skin, and wherein said opening is made in part of the epidermis layer at said blister, and said cultured dermal cells are introduced into the blister cavity.

6. A method as claimed in claim 1 wherein a sheet of epidermis is formed into a pocket and the cultured dermal cells are enclosed inside said pocket of epidermis prior to introduction of said cultured dermal cells through said opening in the epidermis layer.

7. A method as claimed in claim 1 wherein the dermal cells are introduced in the form of a mixture with epidermal cells.

8. A method as claimed in claim 7 wherein said epidermal cells are selected from epidermal cells of interfollicular origin and epidermal cells of intra-follicular origin.

9. A method as claimed in claim 1 wherein said mammal is additionally treated with a hair growth stimulating promoter so as to enhance growth of new hair induced by said introduced cultured dermal cells.

10. A method as claimed in claim 1 wherein said selected dermal cell comprise at least one of dermal papilla and dermal sheath cells.

11. A method as claimed in claim 1 wherein said selected dermal cells are of human scalp origin.

12. A method of treatment of the scalp skin area of a human subject, which area has sufficient hair loss and which has an outer epidermis layer and an inner dermis layer, which method comprises the steps of:
 (a) selecting at least one human scalp lower follicular dermal cell;
 (b) culturing at least one human scalp dermal cell so as to produce cultured dermal cells;
 (c) forming an opening in the outer epidermis layer of said human scalp skin area; and
 (d) introducing said cultured dermal cells through said opening in the epidermis layer into contact with the dermis layer in proximity to the epidermis and with at least some of said cultured dermal cells in contact with epidermal cells.

13. The method of treatment of claim 12 which includes the step of obtaining said at least one lower follicular dermal cell from the scalp of said human subject.

14. The method of treatment of claim 12 which includes the step of obtaining said at least one lower follicular dermal cell from the scalp of another human subject.

* * * * *